US009969769B2

(12) United States Patent
Collins et al.

(10) Patent No.: US 9,969,769 B2
(45) Date of Patent: *May 15, 2018

(54) COUPLING METHOD FOR PEPTIDE SYNTHESIS AT ELEVATED TEMPERATURES

(71) Applicant: CEM CORPORATION, Matthews, NC (US)

(72) Inventors: Jonathan M. Collins, Charlotte, NC (US); Sandeep Kumar Singh, Matthews, NC (US)

(73) Assignee: CEM CORPORATION, Matthews, NC (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/647,909

(22) Filed: Jul. 12, 2017

(65) Prior Publication Data
US 2017/0342104 A1 Nov. 30, 2017

Related U.S. Application Data

(63) Continuation-in-part of application No. 14/969,004, filed on Dec. 15, 2015.

(60) Provisional application No. 62/094,420, filed on Dec. 19, 2014, provisional application No. 62/111,817, filed on Feb. 4, 2015, provisional application No. 62/132,847, filed on Mar. 13, 2015.

(51) Int. Cl.
*C07K 1/00* (2006.01)
*C07K 1/08* (2006.01)
*C07K 1/04* (2006.01)
*C07K 14/575* (2006.01)

(52) U.S. Cl.
CPC ............ *C07K 1/006* (2013.01); *C07K 1/04* (2013.01); *C07K 1/08* (2013.01); *C07K 14/57581* (2013.01)

(58) Field of Classification Search
None
See application file for complete search history.

(56) References Cited

U.S. PATENT DOCUMENTS

| | | | |
|---|---|---|---|
| 4,507,230 A | 3/1985 | Tam | |
| 4,950,418 A | 8/1990 | Yajima | |
| 5,124,478 A | 6/1992 | Breipohl | |
| 6,090,913 A | 7/2000 | Drauz | |
| 8,058,393 B2 | 11/2011 | Collins | |
| 2004/0077827 A1 | 4/2004 | Jackson | |
| 2005/0165217 A1 | 7/2005 | Guinn | |
| 2008/0070884 A1 | 3/2008 | Von Nussbaum | |
| 2013/0072658 A1 | 3/2013 | Prouty | |
| 2014/0088291 A1 | 3/2014 | Takahashi | |
| 2014/0206841 A1 | 7/2014 | Menakuru | |
| 2016/0176918 A1 | 6/2016 | Collins | |

FOREIGN PATENT DOCUMENTS

| | | |
|---|---|---|
| GB | 673639 | 6/1952 |
| GB | 812543 | 4/1959 |
| JP | 2001512139 | 8/2001 |
| JP | 2008518986 | 6/2008 |
| WO | 9906437 | 2/1999 |
| WO | 2004050686 | 6/2004 |
| WO | 2005063791 | 11/2005 |

OTHER PUBLICATIONS

John Pu, Organic Process Research & Development 2009, 13, 310-314 (Year: 2009).*
Dahiya, J. Serb.Chem. Soc. 72 (2) 101-107 (2007) (Year: 2007).*
R. Subiros-Funosas, R. Prohens, R. Barbas, A. El-Faham and F. Albericio, "Oxyma: An Efficient Additive for Peptide Synthesis to Replace the Benzotriazole-Based HOBt and HOAt with a Lower Risk of Explosion," Chemistry Eur. J., vol. 15, pp. 9394-9403, 2009.
Beyermann et al (M. Beyermann, P. Henklein, A. Klose, R. Sohr and M. Bienert, "Effect of tertiary amine on the carbodiimide-mediated peptide synthesis," Int. J. Peptide Protein Res., vol. 37, pp. 252-256, 1991.
Carpino et al; L. Carpino, El-Faham and A., "The Diisopropylcarbodiimide/1-Hydroxy-7-azabenzotriazole System: Segment Coupling and Stepwise Peptide Assembly," Tetrahedron, vol. 55, pp. 6813-6830, 1999.
Collins et al (J. Collins, K. Porter, S. Singh and G. Vanier, "High-Efficiency Solid Phase Peptide Synthesis (HE-SPPS)," Org. Lett., vol. 16, pp. 940-943, Feb. 7, 2014.
Palasek et al (S. Palasek, Z. Cox and J. Collins, "Limiting racemization and aspartimide formation in microwave-enhanced Fmoc solid phase peptide synthesis," J. Pept. Sci., vol. 13, pp. 143-148, 2007.
Perich et al (J. Perich, N. Ede, S. Eagle and A. Bray, "Synthesis of phosphopeptides by the Multipin method: Evaluation of coupling methods for the incorporation of Fmoc-Tyr(PO3Bzl,H)-OH, Fmoc-Ser(PO3Bzl,H)-OH and Fmoc-Thr(PO3Bzl,H)-OH," Lett. Pept. Sci., vol. 6, pp. 91-97, 1999.
X. Shangjie, I. Held, B. Kempf, H. Mayr, W. Steglich and H. Zipse, "The DMAP—Catalyzed Acetylation of Alcohols—A Mechanistic Study," Chemistry, vol. 11, pp. 4751-4757, 2005.
E. Atherton, N. L. Benoiton, E. Brown, R. Sheppard and B. J. Williams, "Racemization of Activaterd, Urethane-protected Aminoacids by p-Dimethylaminopyridine. Significance in Solid-phase Peptide Synthesis," J.C.S. Chem. Comm., pp. 336-337, 1981.
S. Wang, J. Tam, B. Wang and R. Merrifield, "Enhancement of peptide coupling reactions by 4-dimethylaminopyridine," Int. J. Peptide Protein Res., vol. 18, pp. 459-467, 1981.
Pedersen et al., "Microwave heating in solid-phase peptide synthesis," Soc. Rev., 2012, 41, pp. 1826-1844.
Mandity et al., Continuous-Flow Solid-Phase Peptide Synthesis: A Revolutionary Reduction of the Amino Acid Excess; ChemSusChem, 2014, 7, 3172-3176.
M. Pennington, "Procedures to Improve Difficult Couplings," in Peptide Synthesis Protocols, Vols. Methods in Molecular Biology—vol. 35, Totowa, NJ, Humana Press, 1995, p. 10.

(Continued)

*Primary Examiner* — Satyanarayana R Gudibande
(74) *Attorney, Agent, or Firm* — Parsons Summa

(57) ABSTRACT

An improved method for coupling amino acids into peptides or peptidomimetics is disclosed that includes the steps of combining an amino acid, a carbodiimide, an activator additive, and a base at less than 1 equivalent compared to the amino acid to be activated; and carrying out the activation and coupling at a temperature greater than 30° C.

36 Claims, 11 Drawing Sheets

(56) References Cited

OTHER PUBLICATIONS

P. White, J. Collins and Z. Cox, "Comparative study of conventional and microwave assisted synthesis," in 19th American Peptide Symposium, San Diego, CA, 2005.

L. Carpino and A. El-Faham, "Effect of Teriary Bases on O-Benzotriazolyuronium Salt-Induced Peptide Segment Coupling," J. Org. Chem., vol. 59, pp. 695-698, 1994.

M. Cezari and L. Juliano, "Studies on lactam formation during coupling procedures of N alpha-N omega-protected arginine derivatives," J. Pept. Res., vol. 9, pp. 88-91, 1996.

T. Lescrinier, R. Busson, H. Winter, C. Hendrix, G. Janssen, C. Pannecouque, J. Rozenski, A. Aerschot and P. Herdewijn, "a-Amino acids derived from ornithine as building blocks for peptide synthesis," J. Pept. Res., 2011, vol. 49, pp. 183-189.

Subiros-Funosas et al, "Use of Oxyma as pH modulatory agent to be used in the prevention of base-driven side reactions and its effect on 2-chlorotrityl chloride resin," Pept. Sci., vol. 98, pp. 89-97, 2012.

Friligou et al (I. Friligou, E. Papadimitriou, D. Gatos, J. Matsoukas and T. Tselios, "Microwave-assisted solid-phase peptide synthesis of the 60-110 domain of human pleiotrophin on 2-chlorotrityl resin," Amino Acids, vol. 40, pp. 1431-1440, 2011.

Tofteng et al [A. Tofteng, S. Pedersen, D. Staerk and K. Jensen, "Effect of Residual Water and Microwave Heating on the Half-Life of the Reagents and Reactive Intermediates in Peptide Synthesis," Chemistry, vol. 18, pp. 9024-9031, 2012.

Oualid et al., Chemical Synthesis of Ubiquitin, Ubiquitin-Based Probes, and Diubiquitin; Angew. Chem. Int. Ed. 2010, 49, 10149-10153.

Abdelmoty et al., "Structural studies of reagents for peptide bond formation: Crystal and molecular structures of HBTU and HATU," Letters in Peptide Science, 1, 1994, 57-67.

Tam et al., "Chemical Synthesis of Circular Proteins," Journal of Biological Chemistry, vol. 287, No. 32, 2012, pp. 27020-27025.

T. Redemann and G Jung, "In situ Fluoride Activation Allows the Preparation of Peptides not Accessible by Routine Synthesis Protocols," 24th European Pepide Symposium, 1996, 749-750.

Collins et al., High Efficiency Solid Phase Peptide Synthesis (HE-SPPS), Feb. 23, 2014, pp. S1-S11.

Bacsa et al., "Solid-Phase Synthesis of Difficult Peptide Sequences at Elevated Temperatures: A Critical Comparison of Microwave and Conventional Heating Technologies," J Org. Chem., 2008, 73, 7532-7542.

Steinauer et al, Studies on racemization associated with the use of benzotriazol-1-yl-tris (dimethylamino) phosphonium hexafluorophosphate (BOP), Int. J. Peptide Protein Res., 34, 1989, 295-298.

S. Nozaki, "Delay of coupling caused by excess additives," J. Pept. Sci., vol. 12, pp. 147-153, 2006.

K. Wehrstedt, P. Wandrey and D. Heitkamp, "Explosive properties of 1-hydroxybenzotriazoles," J. Hazard Mater, vol. 126, pp. 1-7, 2005.

M. Itoh, "Peptides. IV. Racemization Suppression by the Use of Ethyl-2-Hydroximino-2-cyanoacetate and Its Amide," Bull. Chem. Soc. Jpn., vol. 46, pp. 2219-2221, 1973.

Stryer, Biochemistry, ISBN 0-7167-1843-X; 1988.

* cited by examiner

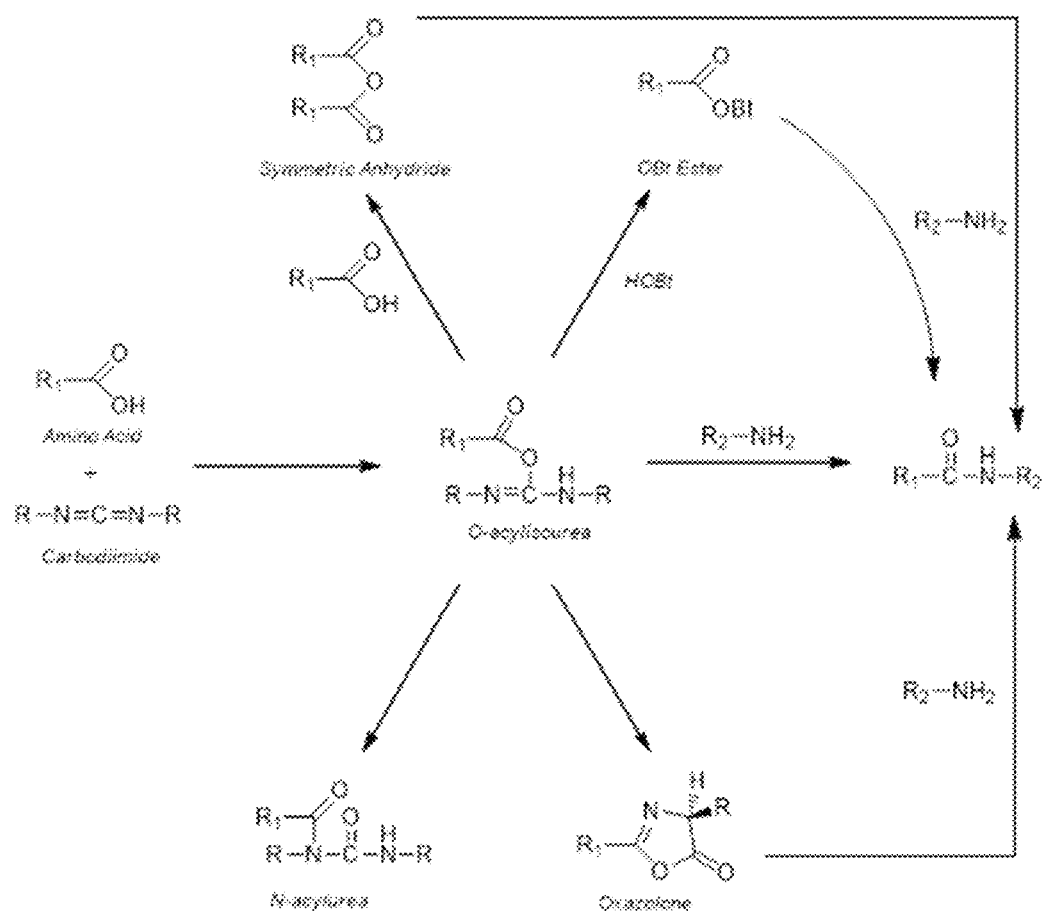
Figure 1 (Prior Art) Carbodiimide Based Activation [2]

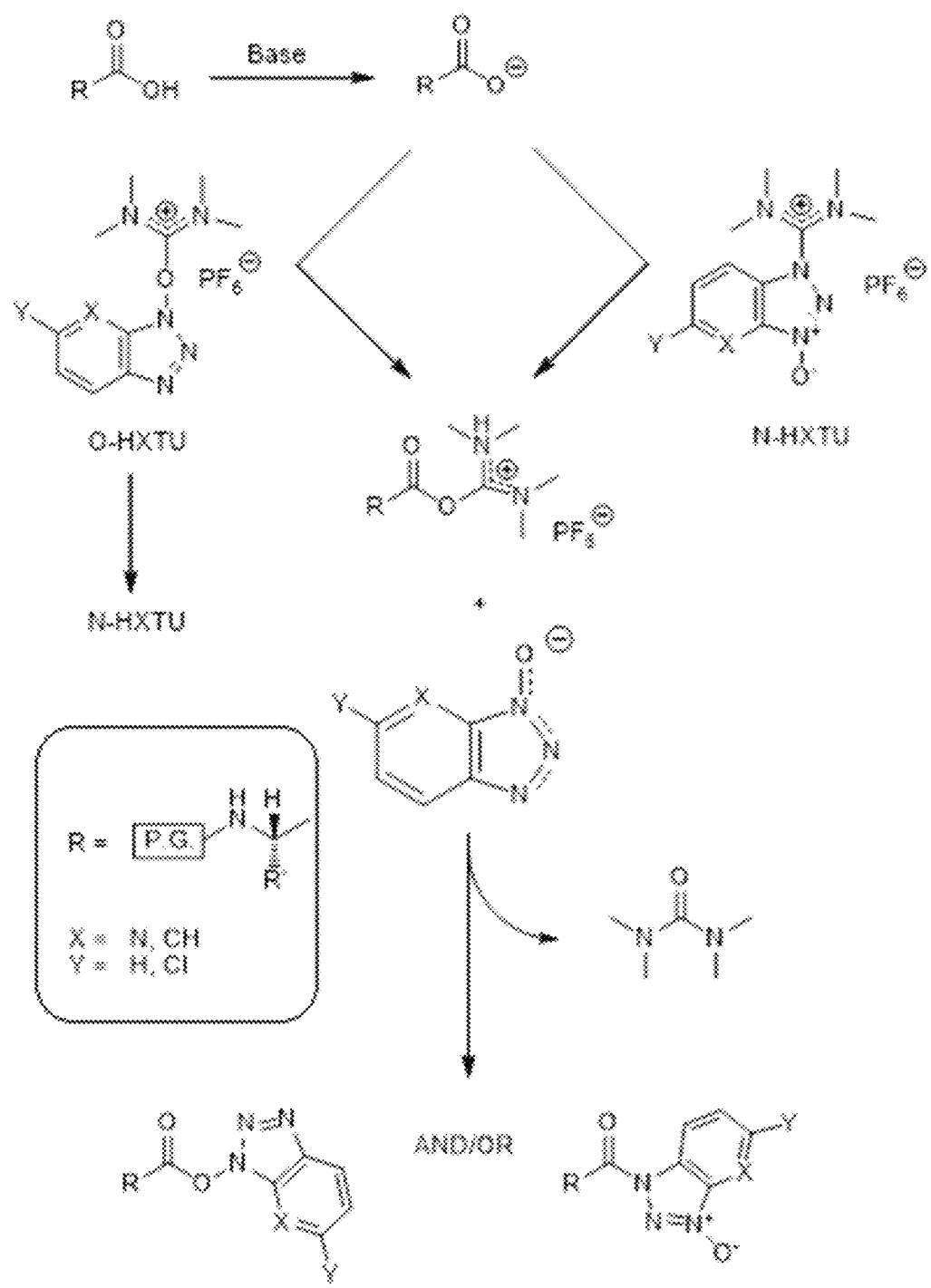
Figure 2 (Prior Art) Onium Salt Based Activation [2]

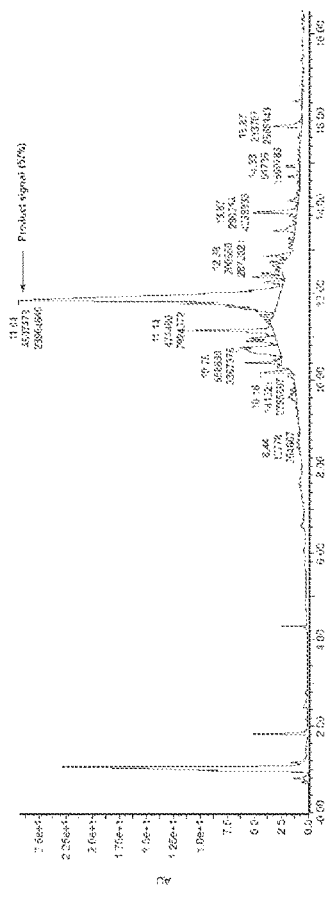
Figure 3 UPLC Chromatogram – Table 1, Entry 5
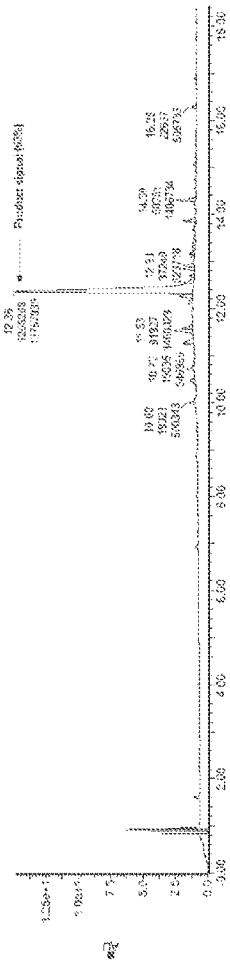
Figure 4 UPLC Chromatogram – Table 2, Entry 3

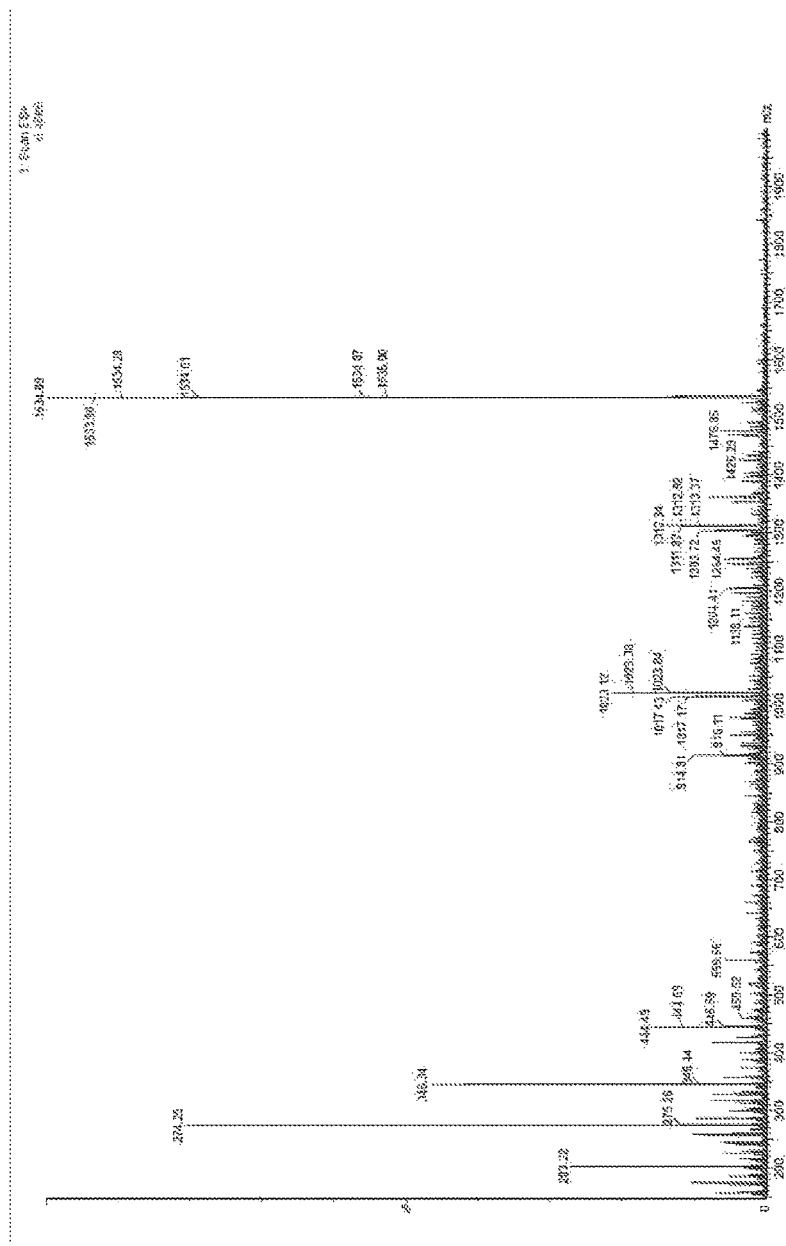
Figure 5 MS Data – Table 2, Entry 3

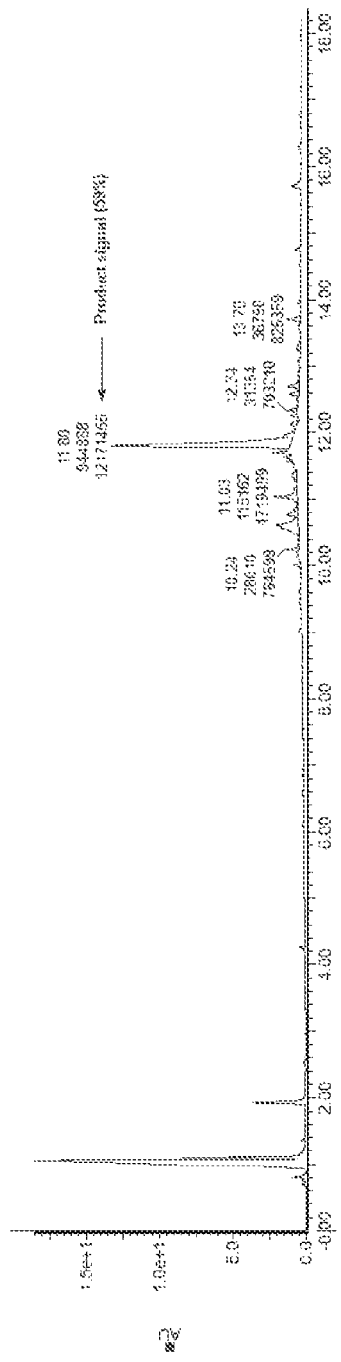
Figure 6 UPLC Chromatogram – Table 2, Entry 5

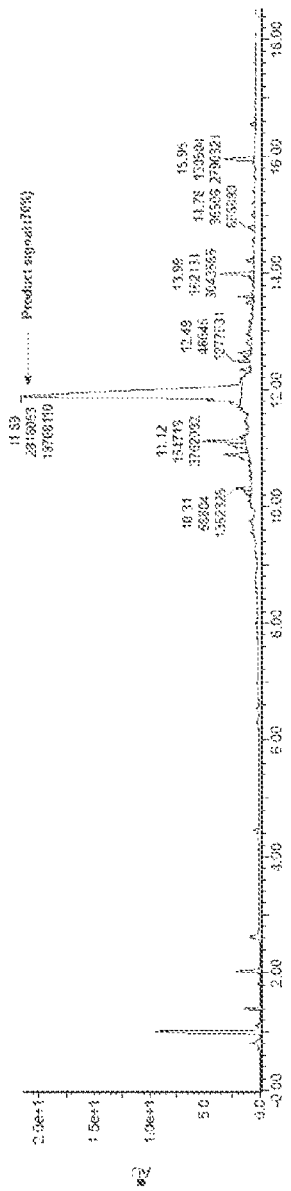
Figure 7 UPLC Chromatogram – Table 3, Entry 2
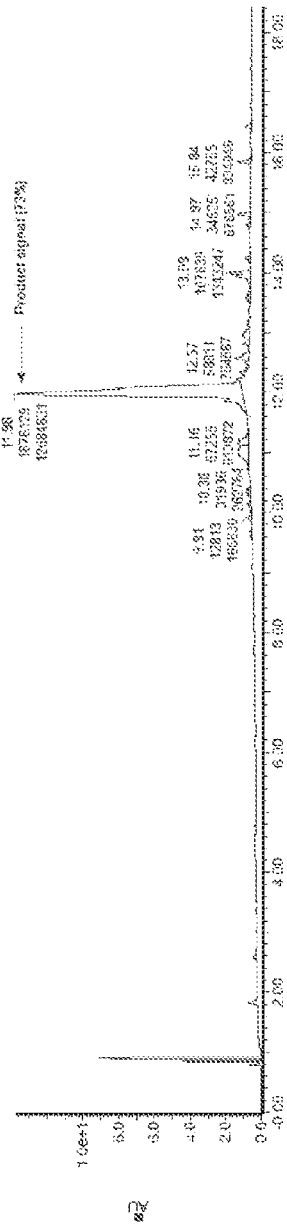
Figure 8 UPLC Chromatogram – Table 3, Entry 5

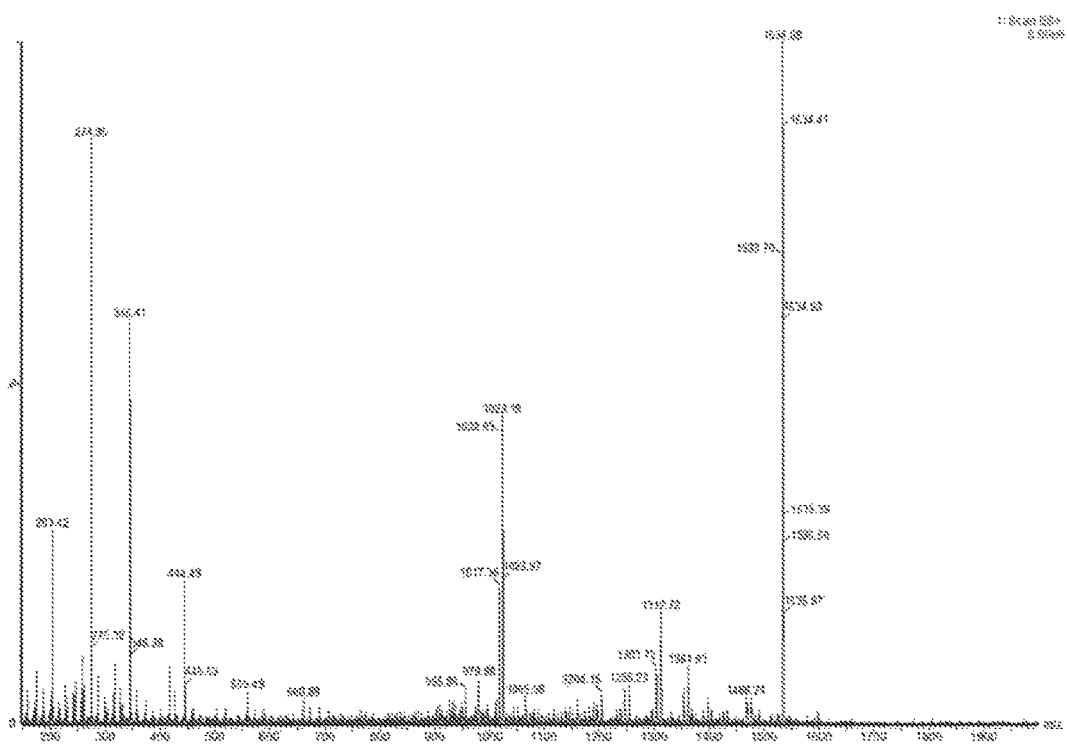
Figure 9 MS Data – Table 3, Entry 5

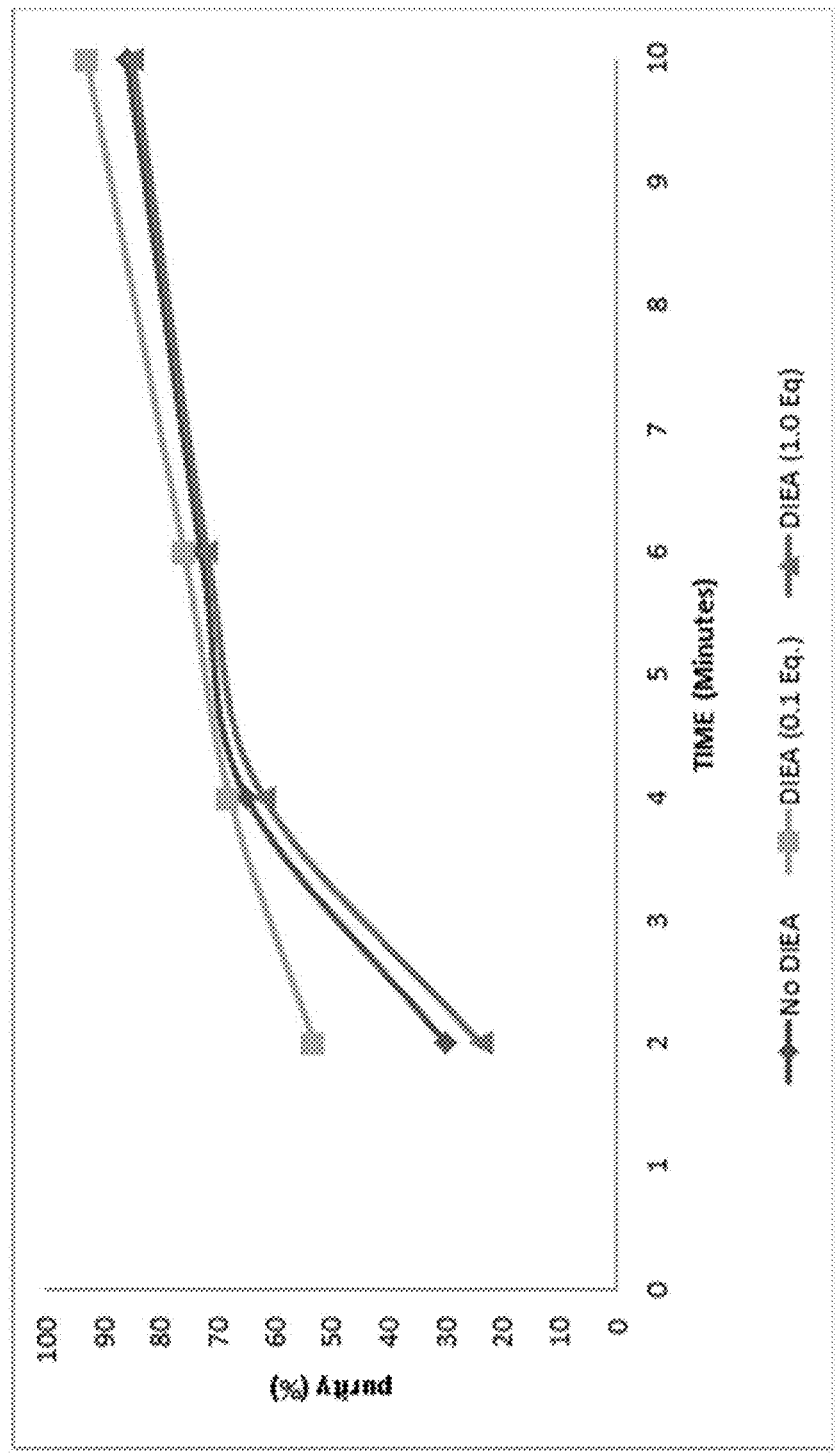

Figure 11 Racemization of activated cysteine OBt ester by direct enolization from a tertiary amine
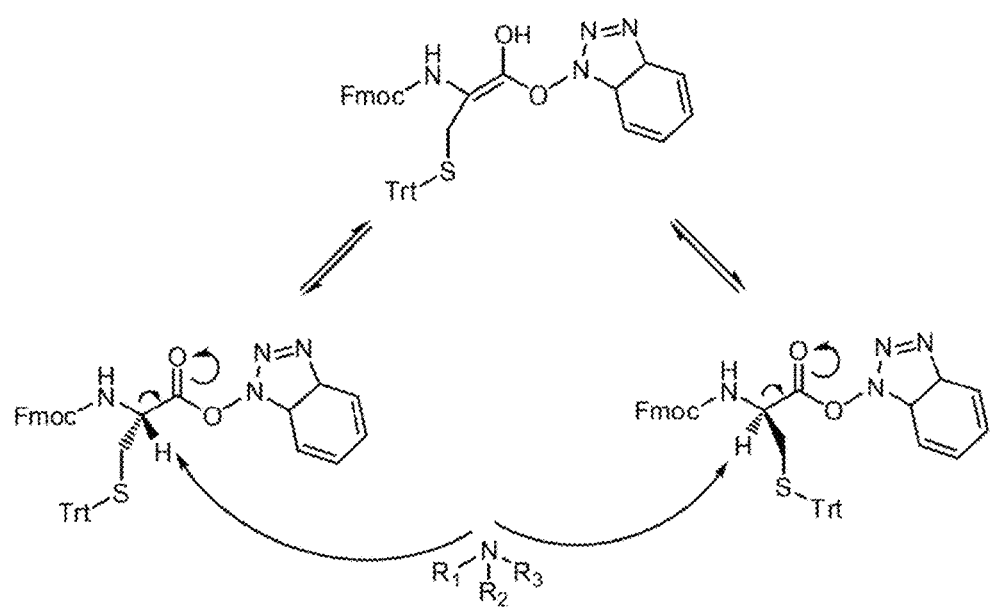
Figure 12 δ-lactam formation with HBTU activation
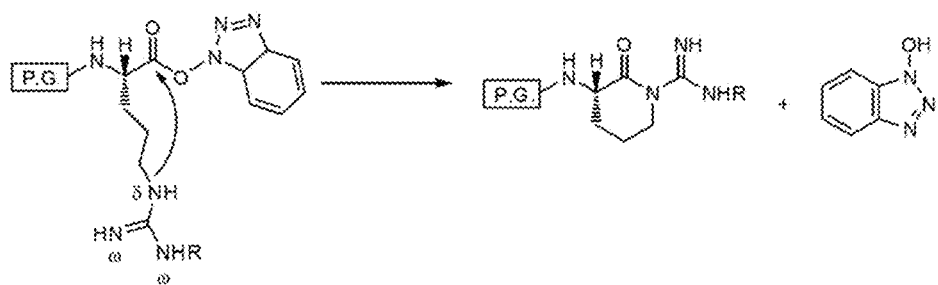

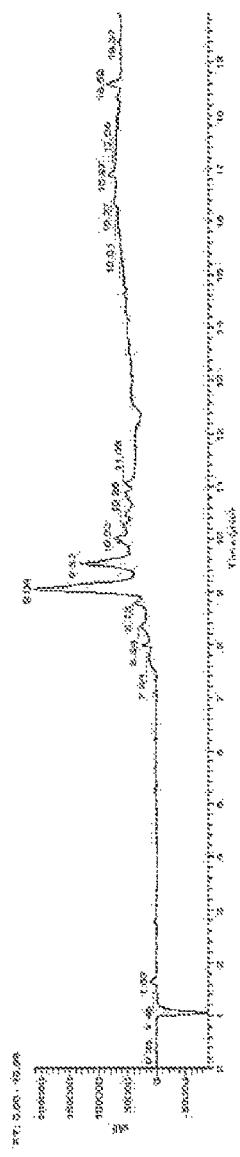
Figure 13 HPLC Chromatogram – Table 7, Entry 1
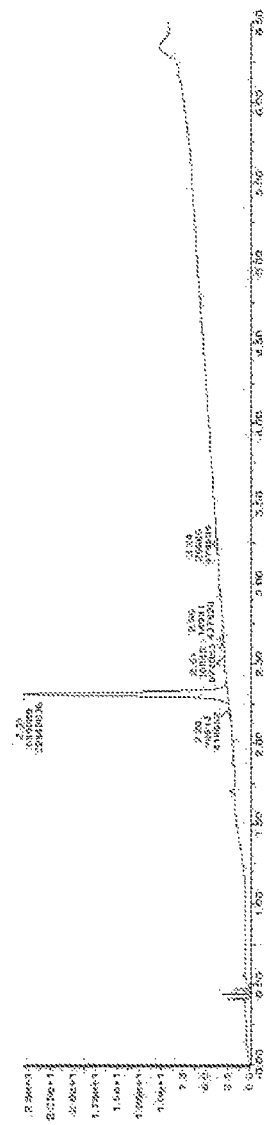
Figure 14 UPLC Chromatogram – Table 7, Entry 2

Figure 15 MS Data – Table 7, Entry 2
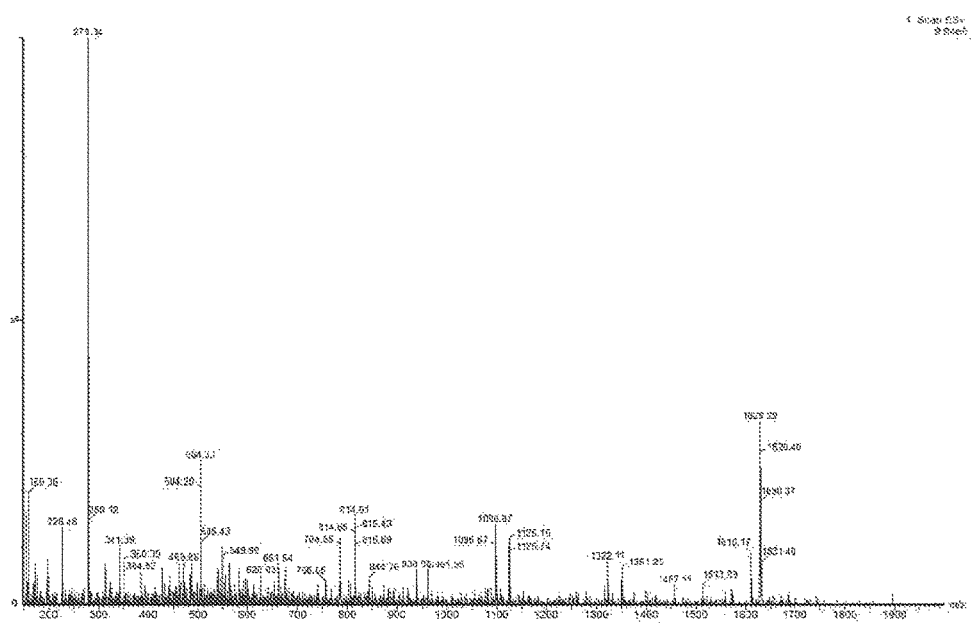
Figure 16 UPLC Chromatogram- Table 7, entry 3
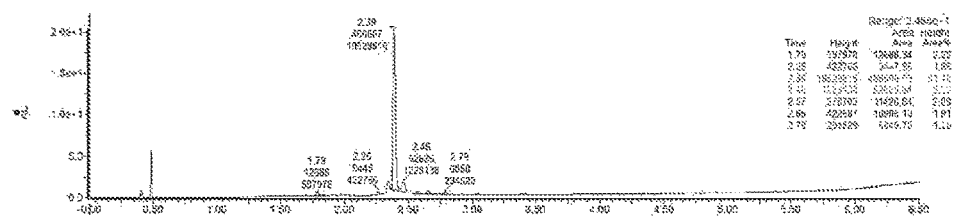

COUPLING METHOD FOR PEPTIDE SYNTHESIS AT ELEVATED TEMPERATURES

BACKGROUND

The invention relates to peptide synthesis and in particular relates to improved activation and coupling in solid phase peptide synthesis ("SPPS") that proceeds at higher rates, generates fewer undesired side reactions, and produces better results.

Solid phase peptide synthesis incorporates several basic steps that are repeated as additional amino acids are added to a growing peptide chain. The "solid phase" refers to resin particles to which initial amino acids—and then the growing peptide chains—are at attached. Because the chains are attached to particles, the chains can be handled as if they were a collections of solid particles (particularly for washing and separation—e.g., filtration—steps), and thus making the overall process easier in many cases than pure solution synthesis.

The repeated steps of SPPS include deprotection, activation and coupling. Deprotection: before each cycle starts, the last acid on the peptide chain remains "protected;" i.e., its "amino" end is connected to a functional group that protects the acid from unwanted reactions. This "protecting group" is thus removed (the "deprotection" step) when the next amino acid is about to be added.

Activation: a compound ("activator") is added to the reaction to produce an intermediate amino acid species that is more likely to couple to the deprotected acid on the peptide chain.

Coupling: the activated species connects to the existing peptide chain.

Carbodiimide Activation Methods

Probably the most commonly used and studied activation method for peptide synthesis is based on the use of carbodiimides. Their use in peptide synthesis dates back to 1955 where N,N'-dicyclohexylcarbodiimide (DCC) was used to facilitate amide bond formation. A carbodiimide contains two slightly basic nitrogen atoms which will react with the carboxylic acid of an amino acid derivative to form a highly reactive O-acylisourea compound as shown in FIG. 1. The formed O-acylisourea can then immediately react with an amine to form a peptide bond; i.e., the path shown horizontally in FIG. 1. Alternatively, the O-acylisourea can or be converted into other reactive species.

Some of these alternative reactions of O-acylisourea, however, promote undesirable pathways that may or may not lead to peptide bond formation, and these undesired pathways are also shown in FIG. 1. Conversion to the unreactive N-acylurea (FIG. 1, lower left) prevents coupling, while epimerization of an activated chiral amino acid can occur through oxazolone formation (lower right). A more desirable highly reactive symmetrical anhydride can be formed by using excess amino acid compared to the carbodiimide (FIG. 1, upper left). This approach, however, undesirably consumes an additional amino acid equivalent.

A significant improvement for carbodiimide activation methods occurred with the incorporation of 1-hydroxybenzotriazole (HOBt) as an additive during carbodiimide activation. HOBt quickly converts the O-acylisourea into an OBt ester (FIG. 1, upper right) that is highly reactive, but avoids undesirable N-acylisourea and oxazolone formation. It was later demonstrated that 1-Hydroxy-7-azabenzotriazole (HOAt) is an advantageous replacement for HOBt due to a neighboring group effect of the nitrogen at the 7-position [161]. Many other additives can be used in place of HOBt and HOAt such as 6-chloro-1-hydroxybenzotriazole (6-Cl-HOBt), ethyl 2-cyano-2-(hydroxyimino)acetate (Oxyma, OxymaPure, ECHA), and 1-hydroxy-2,5-pyrrolidinedione (NHS) to list several common examples.

Typically, 1 equivalent of additive is used compared to the amount of amino acid and carbodiimide. A recent study suggested, however, that reducing the amount of additives to less than 1 equivalent may be useful; S. Nozaki, "Delay of coupling caused by excess additives," *J. Pept. Sci.*, vol. 12, pp. 147-153, 2006. The authors found that the acylation reaction could be hindered by salt formation between the amine and additive. The authors also found, however, that reducing additives to less than 1 equivalent slowed down the activation rate and slightly increased epimerization in segment couplings.

N,N'-Diisopropylcarbodiimide (DIC) has largely replaced DCC as the preferred carbodiimide for peptide activation. DCC undesirably produces a urea soluble only in TFA which in turn makes its use difficult for Fmoc chemistry. Additionally, DCC is a waxy solid that can be difficult to work with and has been reported to cause allergic reactions. Alternatively, DIC offers the advantages of improved solubility of its generated urea in organic solvents, lower incidence of reported allergic reactions, and a relatively low cost. The combination of DIC/HOBt is popular because of its low cost and minimal side reactions while routinely providing effective couplings.

1-ethyl-3-(3-dimethylaminopropyl) carbodiimide ("EDC") represents another popular choice, and a large majority of these reactions are carried out using one or more of DCC, DIC, and EDC.

Recent analysis of benzotriazole based additives such as HOBt, HOAt, and 6-Cl-HOBt have led to their reclassification as class 1 explosives; K. Wehrstedt, P. Wandrey and D. Heitkamp, "Explosive properties of 1-hydroxybenzotriazoles," *J. Hazard Mater*, vol. 126, pp. 1-7, 2005. This undesirable feature of benzotriazole additives has increased interest in developing suitable alternatives for benzotriazole additives such as Oxyma (ethyl 2-cyano-2-(hydroxyimino) acetate; first reported in 1973 (M. Itoh, "Peptides. IV. Racemization Suppression by the Use of Ethyl-2-Hydroximino-2-cyanoacetate and Its Amide," *Bull. Chem. Soc. Jpn.*, vol. 46, pp. 2219-2221, 1973). More recently, the explosive properties of Oxyma were tested by differential scanning calorimetry (DSC) as well as accelerating rate calorimetry (ARC) with favorable results as compared to HOBt; R. Subirós-Funosas, R. Prohens, R. Barbas, A. El-Faham and F. Albericio, "Oxyma: An Efficient Additive for Peptide Synthesis to Replace the Benzotriazole-Based HOBt and HOAt with a Lower Risk of Explosion," *Chemistry*, vol. 15, pp. 9394-9403, 2009.

As another potential disadvantage, the use of carbodiimide based activation methods under room temperature synthesis conditions can lead to high levels of deletions based upon both a relatively slow activation process and a more acidic coupling environment.

Onium Salt Activation

Avoiding the potential disadvantages of DIC activation has led to the more recent development of onium salt based activation methods. Onium salt based activation requires the use of a base which first deprotonates the carboxylic acid to generate a carboxylate anion which in turn reacts with the onium salt activator. Improved coupling has been demonstrated with many onium salts-O-(Benzotriazol-1-yl)-N,N, N',N'-tetramethyluronium hexafluorophosphate (HBTU); 2-(7-Aza-1H-benzotriazole-1-yl)-1,1,3,3-tetramethyluronium hexafluorophosphate (HATU); (Benzotriazol-1-yloxy) tripyrrolidinophosphonium hexafluorophosphate (PyBOP); (3-Hydroxy-3H-1,2,3-triazolo[4,5-b]pyridinato-O)tri-1-pyrrolidinyl-phosphorus hexafluorophosphate (PyAOP); and 2-(6-Chloro-1H-benzotriazole-1-yl)-1,1,3,3-tetramethylaminium hexafluorophosphate (HCTU), among others—compared to carbodiimide based activation under room temperature conditions.

FIG. 2 illustrates onium salt based activation pathways.

Using a Base During Carbodiimide-Type Activation

In a few reports, the presence of a base during carbodiimide based couplings has been investigated under room temperature coupling conditions. Beyermann et al (M. Beyermann, P. Henklein, A. Klose, R. Sohr and M. Bienert, "Effect of tertiary amine on the carbodiimide-mediated peptide synthesis," *Int. J. Peptide Protein Res.*, vol. 37, pp. 252-256, 1991) previously showed that carbodiimide based activation under room temperature conditions is impeded by the presence of a hindered amine base. This can occur from preferential protonation of the base thereby preventing protonation of the carbodiimide; which is a necessary first step in generating the O-acylisourea in carbodiimide based activation techniques. Beyermann et al also showed, however, that the same hindered amine base at 1 equivalent compared to the amino acid could enhance the coupling process at room temperature if it was added after the activation process was completed. In essence, by adding 1 equivalent of base, Beyermann was able to mimic the subsequent acylation conditions of onium salt and carbodiimide activation methods which led to similar results.

Carpino et al; L. Carpino, El-Faham and A., "The Diisopropylcarbodiimide/1-Hydroxy-7-azabenzotriazole System: Segment Coupling and Stepwise Peptide Assembly," *Tetrahedron*, vol. 55, pp. 6813-6830, 1999 later showed that the presence of a significantly weaker base such as 2,4,6-trimethylpyridine (TMP) at 1 or 2 equivalents relative to the amino acid in carbodiimide based couplings can improve both the activation and coupling steps without interfering with the protonation of the carbodiimide. In the same study, Carpino et al (1999) also showed that the use of the stronger base DIEA at 3 or 4 equivalents to the amino acid was significantly more effective in the subsequent peptide acylation step than the weaker base TMP in a difficult 5-mer sequence. Carpino et al (1999) also showed (in agreement with Beyermann et al) that the presence of a strong base hinders the activation process and thus should only be present during the subsequent acylation step.

Thus, both Carpino et al (1999) and Beyermann et al teach that in some cases, room temperature carbodiimide based coupling methods can produce optimal results by using a pre-activation step followed by subsequent acylation in the presence of a strong base such as DIEA present in an amount of 1-4 equivalents relative to the activated amino acid. As a rationale, using at least 1 equivalent of base compared to the activated amino acid mimics onium salt based techniques where 2 equivalents of base are typically used. In the onium salt case, the first equivalent is required for carboxylate anion formation necessary during activation while the second equivalent is present for enhancing the subsequent acylation step.

Nevertheless, Beyermann et al notes that this method only matches the synthesis results observed with onium salts (BOP, TBTU) while Carpino (1999) does not make a direct comparison between onium salt coupling and a carbodiimide based coupling in the presence of a base. Thus, together Carpino (1999) and Beyermann et al teach that the acylation step after a carbodiimide based activation can be made to perform similarly to an acylation step after an onium salt based activation by incorporating a similar amount of base at room temperature.

The use of bases during the coupling process is, however, less than ideal because they can lead to undesirable side reactions. Collins et al (J. Collins, K. Porter, S. Singh and G. Vanier, "High-Efficiency Solid Phase Peptide Synthesis (HE-SPPS)," *Org. Lett.*, vol. 16, pp. 940-943, 2014) showed minimal cysteine epimerization at 90° C. under a carbodiimide based coupling method without the presence of any base. Palasek et al (S. Palasek, Z. Cox and J. Collins, "Limiting racemization and aspartimide formation in microwave-enhanced Fmoc solid phase peptide synthesis," *J. Pept. Sci.*, vol. 13, pp. 143-148, 2007) showed that significant cysteine epimerization can occur under onium salt activation methods when DIEA and NMM are present at 2 equivalents. Furthermore the Fmoc protecting group is slowly labile to DIEA, and this lability can increase at higher temperatures leading to undesirable insertion sequences (which can be difficult to separate).

In a separate study, Perich et al (J. Perich, N. Ede, S. Eagle and A. Bray, "Synthesis of phosphopeptides by the Multipin method: Evaluation of coupling methods for the incorporation of Fmoc-Tyr(PO3Bzl,H)—OH, Fmoc-Ser(PO3Bzl, H)—OH and Fmoc-Thr(PO3Bzl,H)—OH," *Lett. Pept. Sci.*, vol. 6, pp. 91-97, 1999) compared DIC/HOBt (1:1) and DIC/HOBt/DIEA (1:1:1) activation systems to various onium salt methods in the room temperature synthesis of three 10mer phosphopeptides. They concluded that both carbodiimide methods are inferior to HBTU/HOBt/DIEA and HATU/HOAt/DIEA.

Linking and Cleavage

A fundamental initial step in SPPS is, of course, that of connecting ("linking") the first amino acid to the selected polymer resin using an intermediate compound ("linker") to do so. This initial linking step can require particular conditions. Such modified conditions are typically required for standard acid linkers that feature a hydroxyl group which must act as a nucleophile for coupling. Acetylation of alcohols is difficult and is typically facilitated by 4-dimethylaminopyridine (DMAP) which acts as an acetylation catalyst for alcohols; [X. Shangjie, I. Held, B. Kempf, H. Mayr, W. Steglich and H. Zipse, "The DMAP-Catalyzed Acetylation of Alcohols—A Mechanistic Study," *Chemistry*, vol. 11, pp. 4751-4757, 2005. Exemplary acid linkers include the widely used HMPA and Wang linkers among others. In these instances, a modified carbodiimide based coupling technique has been used where a highly reactive symmetrical anhydride is generated in the absence of additives (ex. HOBt, HOAt, and Oxyma) and with 1 equivalent or less of DMAP added to facilitate coupling. DMAP should be avoided during the activation process because it tends to dramatically slow activation (as shown by Carpino et al and others). This procedure is well known and described in the literature (E. Atherton, N. L. Benoiton, E. Brown, R. Sheppard and B. J. Williams, "Racemization of Activaterd, Urethane-protected Amino-acids by p-Dimethylaminopyridine. Significance in Solid-phase Peptide Synthesis," *J.C.S. Chem. Comm.*, pp. 336-337, 1981; S. Wang, J. Tam, B. Wang and R. Merrifield, "Enhancement of peptide coupling reactions by 4-dimethylaminopyridine," *Int. J Peptide Protein Res.*, vol. 18, pp. 459-467, 1981; M. Pennington, "Procedures to Improve Difficult Couplings," in *Peptide Synthesis Protocols*, Vols. Methods in Molecular Biology—vol. 35, Totowa, N.J., Humana Press, 1995, p. 10). Unfortunately, the method is known to cause extensive epimerization even at room temperature and is problematic for loading (linking) sensitive amino acid derivatives such as cysteine and histidine onto resins.

Heating, Elevated Temperatures, and Microwave Irradiation

As another factor, in recent years a heating step or a microwave irradiation step during SPPS has been extensively applied as a method to improve SPPS and amino acid coupling. Microwave irradiation or other known conventional heating methods have been used with both standard carbodiimide and onium salt coupling processes. Using elevated temperature during the coupling step, however, presents several challenges for peptide synthesis. During onium salt based activation methods epimerization of cysteine derivatives is substantially increased. This epimerization results from the presence of the base (typically DIEA, NMM) at elevated temperatures. Additionally, increased δ-lactam formation of arginine during activation has been observed and leads to major arginine deletions in certain sequences; P. White, J. Collins and Z. Cox, "Comparative study of conventional and microwave assisted synthesis," in 19th American Peptide Symposium, San Diego, Calif., 2005.

Recently, Collins et al (J. Collins, K. Porter, S. Singh and G. Vanier, "High-Efficiency Solid Phase Peptide Synthesis (HE-SPPS)," Org. Lett., vol. 16, pp. 940-943, 2014) showed that very rapid and efficient couplings could be performed by in-situ carbodiimide based couplings at 90° C. without any base. This demonstrated that microwave irradiation is capable of accelerating both the slow activation process and subsequent acylation step in 2 minutes at 90° C. Avoiding any base present during the Collins coupling process offered the advantages that activation was not hindered in the manner described by Carpino (1999) and Beyermann et al and that the coupling environment was safer from epimerization. In fact Collins et al showed that Fmoc-Cys (Trt)-OH could be coupled at 90° C. without an increase in epimerization compared to room temperature methods. Therefore, Collins et al (J. Collins, K. Porter, S. Singh and G. Vanier, "High-Efficiency Solid Phase Peptide Synthesis (HE-SPPS)," Org. Lett., vol. 16, pp. 940-943, 2014) teaches that an optimal use of carbodiimide chemistry at elevated temperatures avoids the use of bases.

As a disadvantage, however, the more acidic environment at higher temperatures required to drive the less reactive carbodiimide activation (compared to onium salts) tends to lead to premature cleavage of peptides attached to hyper-acid sensitive linkers (e.g., 2-chlorotrityl). Such premature cleavage can result in total loss of peptide from the resin and can significantly limit the temperatures that can be applied with this class of linkers.

Hyper-acid sensitive linkers are, however, of major importance in peptide synthesis because they allow for peptide fragment condensation which allows for larger peptide sequences to be constructed. Bulky hyper-acid linkers (such as 2-chlorotrityl) are also uniquely important for avoiding important side reactions such as diketopiperazine formation, avoiding DMAP during resin loading, and beta-elimination of c-terminal cysteine residues connected to acid linkers.

In brief and potentially partial summary, the advantages of higher temperature or microwave-assisted SPPS are offset by several disadvantages. As one disadvantage, the combination of a DIC activator, an acidic environment, and certain resins leads to (i) early (undesired) cleavage; and (ii) slower coupling after activation.

As an alternative disadvantage, an onium activator requires at least one equivalent of base to add each acid, but the extra-base will tend to racemize some acids and will degrade others.

As a third potential disadvantage, bases affect the stability of amino acids at high temperature; a factor that reduces the reaction time window, particularly for certain acids such as arginine.

Therefore, a peptide chemist faces numerous, and sometimes competing, limitations when applying elevated temperature to the coupling step in peptide synthesis with either carbodiimide or onium salt based activation methods.

SUMMARY

The invention is an improved coupling method for SPPS which overcomes the limitations of coupling with both standard carbodiimide and onium salt based methods at elevated temperatures. This method is a modified carbodiimide activation strategy which features the use of a base. A strong base added at less than (no more than) 1-equivalent compared to the amino acid can be present during the entire activation and coupling process while enhancing the overall coupling reaction, avoiding potential side reactions, enhancing the synthesis speed, and increasing the purity of the resulting peptide.

In one aspect, the improvement includes the steps of combining an amino acid, a carbodiimide, an activator additive, and a base, with the base in an amount of less than (i.e., no more than) one equivalent as compared to the amount of amino acid to be activated, and carrying out the activation and coupling steps at a temperature greater than 30° C.

In another aspect, the invention is an improvement in the method of coupling carboxylic acids and amines. The improvement includes the steps of combining a carboxylic acid, an amine, a carbodiimide, an activator additive, and a base, with the base in an amount of less than 1 equivalent compared to the amine; and carrying out activation and coupling at a temperature greater than 30° C.

In yet another aspect, the improvement includes the steps of combining a hyper-acid sensitive linker (connecting a peptide and a solid phase resin), an amino acid, a carbodiimide, an activator additive, and a base; and carrying out the activation and coupling at an elevated temperature greater than 30° C.

BRIEF DESCRIPTION OF THE DRAWINGS

The foregoing and other objects and advantages of the invention and the manner in which the same are accomplished will become clearer based on the followed detailed description taken in conjunction with the accompanying drawings.

FIG. 1 is an illustration of the well understood possible pathways for carbodiimide based activation.

FIG. 2 is a diagram of the well understood reaction pathways for onium salt based activation.

FIG. 3 is a UPLC (ultra performance liquid chromatography) chromatogram from a Thymosin synthesis carried out at 90° C. following an onium salt activation in the presence of 2 equivalents of base.

FIG. 4 is a UPLC chromatogram from a Thymosin synthesis carried out at 90° C. in the presence of Oxyma, but without any base.

FIG. 5 is a mass spectrum from a Thymosin synthesis carried out at 90° C. in the presence of Oxyma, but without any base.

FIG. 6 is a UPLC chromatography gram from a Thymosin synthesis carried out at 90° C. in the presence of Oxyma and one equivalent of base.

FIG. 7 is a UPLC chromatogram from a Thymosin synthesis carried out at 90° C. with Oxyma and in the presence of 0.1 equivalents of base.

FIG. 8 is a UPLC chromatogram from a Thymosin synthesis carried out at 100 C with Oxyma and in the presence of 0.1 equivalent of base.

FIG. 9 is a mass spectrum from a Thymosin synthesis carried out at 100° C. with Oxyma and in the presence of 0.1 equivalent of base.

FIG. 10 is a plot comparing peptide purity to the amount of base included for a coupling reaction carried out at 90° C.

FIG. 11 illustrates one racemization pathway for cysteine in solid phase peptide synthesis.

FIG. 12 illustrates a potential lactam formation reaction in SPPS that is specific to arginine.

FIG. 13 is an HPLC (high pressure liquid chromatography) chromatogram of ABRF 1992 peptide carried out at 90° C. using HBTU and two equivalents of base.

FIG. 14 is a UPLC chromatogram of ABRF 1992 peptide carried out at 90° C. using DIC and Oxyma, but without any base.

FIG. 15 is the mass spectrum of the same reaction as FIG. 14.

FIG. 16 is a UPLC chromatogram of the same reaction as FIG. 14, but using 0.1 equivalent of base.

DETAILED DESCRIPTION

In a broad sense, the invention incorporates a base in a manner that improves SPPS carried out at elevated temperature. Potentially, many different types of bases could be used for this process. As used herein, phrases such as "1 equivalent of base" or "0.1 equivalent of base" will always refer to the amount of base present as compared to the amount of amino acid present, unless some other meaning is clearly indicated in context. In addition to the bases set forth in the accompanying examples, Applicants believe that trimethylamine ("TEA") will be useful in the same or similar circumstances.

Additionally, those of skill in this art will recognize that the invention and its advantages can be expressed in terms of the reaction of a carboxylic acid and an amine.

A limitation of onium salt based methods is that they require at least 1 equivalent of base compared to the amino acid and activator to complete activation. This is because a carboxylate anion must be generated on each amino acid to be activated so that it can perform a nucleophilic attack on the onium salt activator as shown in FIG. 2. We verified the need for the base by synthesizing a known difficult 28 mer peptide (Thymosin) with various amounts of base (DIEA) as shown in Table 1. FIG. 3 is the UPLC chromatogram for the experiment that used HBTU for activation and 2 equivalents of DIEA as the base (Entry 5). FIG. 3 shows many (undesired) fragments and an overall lack of purity.

TABLE 1

Synthesis of Thymosin with Onium Salt Activation at Various Base Equivalents

| Entry | Temp (° C.) | Coupling Time | Activation | DIEA (Equivalents) | % Purity (UPLC-MS) |
|---|---|---|---|---|---|
| 1 | 75 | 5 | HBTU/DIEA | 2 | 44 |
| 2 | 75 | 5 | HCTU/DIEA | 2 | 39 |
| 3 | 75 | 5 | HATU/DIEA | 2 | 35 |
| 4 | 90 | 2 | HCTU/DIEA | 2 | 56 |
| 5 | 90 | 2 | HBTU/DIEA | 2 | 57 |
| 6 | 90 | 2 | HBTU/DIEA | 1 | 39 |
| 7 | 90 | 2 | HBTU/DIEA | 0.5 | 14 |
| 8 | 90 | 2 | HBTU/DIEA | 0.1 | 0 |

Experiment Conditions:

Peptide Sequence (Thymosin)=SDAAVDTSSEITT-KDLKEKKEVVEEAEN-NH$_2$

Synthesis Scale=0.1 mmol

Resin=Rink Amide MBHA Polystyrene Resin (0.38 mmol/g)

Instrument=Liberty Blue Microwave Peptide Synthesizer (CEM Corp., Matthews, N.C.)

Deprotection=3 mL of a 10% (w/v) piperazine in EtOH:NMP (1:9)

Microwave Deprotection Method=1 min at 90° C.

Washing=Post-Deprotection (2 mL, 2 mL, 3 mL-DMF); Post-Coupling=None

Coupling=5-fold excess of AA/HBTU/DIEA (1:0.9:variable) in 4 mL solution

Cleavage=5 mL of TFA/TIS/H$_2$O/DODt (92.5:2.5:2.5:2.5) for 30 min at 38° C. in an Accent MW cleavage system (CEM Corp., Matthews, N.C.)

Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

In contrast, this same peptide (Thymosin) could be synthesized at higher purity (63%; Table 2, Entry 11) without the presence of any base using carbodiimide based activation (DIC) and the common activator additive Oxyma.

We then investigated the addition of bases during the entire activation and subsequent acylation step at 1 to 2 equivalents compared to the amino acid to be activated. These approaches resulted in either a decrease or similar purity compared to the control experiment without base.

Beyermann et al and Carpino (1999) have suggested that the purity could be somewhat increased by adding the base after activation is complete, and described how formation of the O-acylisourea can be hindered by the presence of a strong base under room temperature conditions. Adding the base after activation, however, increases the complexity of potential automation and is also difficult to perform without slowing down the overall coupling process and increasing the manipulative steps required (which can increase the complexity of any corresponding automation step). Additionally, at the elevated temperatures used in these experiments, we did not observe a significant benefit from the presence of TMP during the entire coupling process. In comparison, Carpino (1999) used TMP under room temperature conditions to offer improvements for carbodiimide based coupling processes.

TABLE 2

Synthesis of Thymosin with Carbodiimide Activation and zero or at least 1 Equivalents of Base

| Entry | Temp (° C.) | Coupling Time | Additive | Base (Equivalents) | % Purity (UPLC-MS) |
|---|---|---|---|---|---|
| 1 | 60 | 5 | HOBt | None | 38 |
| 2 | 60 | 5 | Oxyma | None | 52 |
| 3 | 90 | 2 | Oxyma | None | 63 |
| 4 | 90 | 4 | Oxyma | None | 67 |
| 5 | 90 | 2 | Oxyma | DIEA-(1) | 59 |
| 6 | 90 | 2 | Oxyma | DIEA-(2) | 55 |
| 7 | 90 | 2 | Oxyma | NMM-(1) | 64 |
| 8 | 90 | 2 | Oxyma | NMM-(2) | 49 |
| 9 | 90 | 2 | Oxyma | TMP-(1) | 63 |
| 10 | 100 | 2 | Oxyma | None | 61 |
| 11 | 110 | 2 | Oxyma | None | 63 |

Experiment Conditions:
Peptide Sequence (Thymosin)=SDAAVDTSSEITT-KDLKEKKEVVEEAEN-NH$_2$
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) piperazine in EtOH:NMP (1:9)
Microwave Deprotection Method=1 min at 90° C.
Washing=Post-Deprotection (2 mL, 2 mL, 3 mL-DMF); Post-Coupling=None
Coupling=5-fold excess of AA/DIC/Additive (1:1:1) in 4 mL solution
Cleavage=5 mL of TFA/TIS/H$_2$O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

FIGS. 4 and 6 are respective chromatograms from Table 2 and FIG. 5 is a mass spectrum corresponding to the experiment of FIG. 4. These demonstrate generally similar performance as between no base (63% in FIG. 4) and 1 equivalent of base (59% in FIG. 6) for carbodiimide based coupling at elevated temperatures.

In favorable comparison to prior art efforts, the use of the invention raised the purity up to 73% by using only small amounts of base (DIEA), and specifically much less than 1 equivalent as compared to the amount of amino acid and carbodiimide activator. Using the invention, the presence of a base at a low excess does not significantly hinder O-acylisourea formation at elevated temperature and simultaneously improves the subsequent acylation step.

Table 3 categorizes some of these results at elevated temperatures and using several different amounts of base, but all at less than one equivalent.

TABLE 3

Synthesis of Thymosin with Carbodiimide Activation and less than 1 Base Equivalent

| Entry | Coupling Temp (° C.) | Coupling Time | Base (Equivalents) | % Purity (UPLC-MS) |
|---|---|---|---|---|
| 1 | 90 | 2 | DIEA-0.05 | 61 |
| 2 | 90 | 2 | DIEA-0.1 | 70 |
| 3 | 90 | 2 | DIEA-0.4 | 70 |
| 4 | 90 | 2 | DIEA-0.8 | 67 |
| 5 | 100 | 2 | DIEA-0.1 | 73 |
| 6 | 110 | 2 | DIEA-0.1 | 73 |

Experiment Conditions:
Peptide Sequence (Thymosin)=SDAAVDTSSEITT-KDLKEKKEVVEEAEN-NH$_2$
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) piperazine in EtOH:NMP (1:9)
Microwave Deprotection Method=1 min at 90° C.
Washing=Post-Deprotection (2 mL, 2 mL, 3 mL-DMF); Post-Coupling=None
Coupling=5-fold excess of AA/DIC/Oxyma (1:1:1) in 4 mL solution
Cleavage=5 mL of TFA/TIS/H$_2$O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

FIGS. 7, 8 and 9 are UPLC chromatograms and a mass spectrum from the Table 3 results and demonstrate the improvements of the invention for the synthesis of Thymosin at various temperatures. FIG. 7 shows 70% purity using 0.1 equivalent of base at 90° C.; FIG. 8 shows 73% purity using 0.1 equivalent of base at 100° C.; and FIG. 9 is the mass spectrum of the experiment of FIG. 8.

The ability to achieve these improvements in synthesis with the presence of only a very small amount of base is surprising and uniquely valuable. Because larger amounts of base have been shown to drive the acylation reaction to completion under room temperature conditions, the small amounts of base used in the invention are counter-intuitive. In fact, Carpino (1999) demonstrated that a difficult acylation reaction improved as the amount of base (DIEA) present was increased up to 4 equivalents during the room temperature synthesis of a difficult peptide.

Although the inventors do not wish to be bound by any theory, it appears that the results from the present invention may result from the effect of elevated temperature on the stability of an activated amino acid derivative. To evaluate this possibility we carried out a set of experiments using a pre-activated representative Fmoc amino acid at various elevated temperature conditions. Immediately after pre-activating for a designed time interval, the activated amino acid derivative was cooled to room temperature and then added at 1 equivalent to a 4 mer peptide on a resin under similar conditions in all cases. This demonstrated the amount of activated amino acid that survived the activation process at high temperatures to in turn demonstrate the relative stability.

As shown in Table 4, at elevated temperatures there exists a negative correlation between the stability of the activated amino acid derivative and the amount of base present. This shows that higher amounts of base present in the coupling reaction lead to faster destruction of the activated amino acid species thereby reducing subsequent acylation efficiency. It should be noted that the acylation process regenerates the acidic activator additive. Therefore, the activated amino acid species should have a somewhat longer lifetime in an in-situ activation process where the acidic additive is generated simultaneously with activation, and thus would partially offset the presence of base.

TABLE 4

Stability of activated amino acid esters in the presence of base from various pre-activation conditions

| Entry | Pre-activation (2 min/90° C.) 1.0 equiv. active ester | Base (Equivalents) | H₂O Added (mL) | Activation Temp (° C.) | Activation Time (min) | % Coupled (UPLC-MS) |
|---|---|---|---|---|---|---|
| 1 | Amino Acid/PyAOP (1:1) | DIEA (2) | None | 90 | 2 | 1 |
| 2 | Amino Acid/PyAOP (1:1) | DIEA (1) | None | 90 | 2 | 40 |
| 3 | Amino Acid/DIC/Oxyma (1:1:1) | None | None | 90 | 2 | 90 |
| 4 | Amino Acid/DIC/Oxyma (1:1:1) | None | 0.5 mL | 90 | 2 | 36 |
| 5 | Amino Acid/DIC/Oxyma (1:1:1) | None | None | 110 | 2 | 48 |
| 6 | Amino Acid/DIC/Oxyma (1:1:1) | DIEA (1) | None | 90 | 2 | 22 |
| 7 | Amino Acid/DIC/Oxyma (1:1:1) | DIEA (1) | 0.5 mL | 90 | 2 | 5 |
| 8 | Amino Acid/DIC/Oxyma (1:1:1) | DIEA (0.1) | None | 90 | 2 | 44 |
| 9 | Amino Acid/DIC/Oxyma (1:1:1) | DIEA (0.1) | 0.5 mL | 90 | 2 | 38 |
| 10 | Amino Acid/DIC/Oxyma (1:1:1) | NMM (2) | None | 90 | 2 | 24 |
| 11 | Amino Acid/DIC/Oxyma (1:1:1) | TMP (1) | None | 90 | 2 | 47 |

Experiment Conditions:
Peptide Sequence=DYING-NH₂
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) piperazine in EtOH:NMP (1:9)
Microwave Deprotection Method=1 min at 90° C.
Washing=Post-Deprotection (2 mL, 2 mL, 3 mL-DMF); Post-Coupling=None
Coupling (for all amino acids except Fmoc-Asp(OtBu)-OH=5-fold excess of AA/DIC/Oxyma (1:1:1) in 4 mL solution
Coupling (Fmoc-Asp(OtBu)-OH)=The amino acid was pre-activated as described in Table 4 and cooled to room temperature before coupling. Subsequent coupling was performed for 2 min at 90° C.
Cleavage=5 mL of TFA/TIS/H₂O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)
Water
Tofteng et al [A. Tofteng, S. Pedersen, D. Staerk and K. Jensen, "Effect of Residual Water and Microwave Heating on the Half-Life of the Reagents and Reactive Intermediates in Peptide Synthesis," *Chemistry*, vol. 18, pp. 9024-9031, 2012] recently examined the influence of water on the stability of activated amino acids in water. The authors noted a correlation between the stability of certain coupling reagents and activated esters based on varying amounts of water (from 50-18,000 ppm) in DMF. Additionally, the authors compared the efficiency of DIC/Oxyma/DIEA (1:1:2) versus DIC/Oxyma (1:1) and observed no significant difference in the synthesis purity of a 10 mer peptide.

We found that even in the presence of large amounts of water (e.g., more than 300,000 ppm) an activated ester was still 36% intact after 2 min at 90° C. (Table 4, entry 4) versus 90% intact without additional water added (Table 4, entry 3). This difference suggested that the ester has higher stability in the presence of more than 300,000 ppm of water than in the absence of any additional water, but in the presence of 1 equivalent of DIEA (Table 4, entry 6). The presence of more than 300,000 ppm and 1 equivalent of DIEA (Table 4, entry 7) displayed only a 5% survival rate.

An onium salt based coupling provided further indication of the instability of an activated ester at elevated temperature in the presence of a base. An ester generated from the onium salt PyAOP was only 1% intact after 2 min at 90° C. in the presence of 2 equivalents of base (Table 4, entry 1). The stability could be increased to 40% (Table 4, entry 2) by reducing the base equivalents to 1. This method (no added water) was ineffective, however, in synthesizing the difficult Thymosin sequence (Table 1, entry 6).

Without being bound by theory, these results indicate that the presence of a base during the coupling process is a primary factor affecting stability of an activated amino acid species at elevated temperature. The pH is strongly affected by a strong non-nucleophilic base (such as DIEA, or trimethylamine; "TEA") which can accelerate destruction of an activated amino acid species. Specifically, the non-nucleophilic nature of a tertiary amine can attract protons from any water present, which in turn generates hydroxide (OH$^{-1}$) ions. These hydroxide ions rapidly (and undesirably) hydrolyze the activated esters, thus quenching the desired coupling. Secondarily, the non-nucleophilic base can catalyze attack from amines present in the solvent (e.g., dimethylamine). Additionally, the hindrance of the base may also affect its destructive impact on the activated species. For example, the base NMM is significantly weaker than DIEA, but is less hindered. These factors together appear to cause NMM to reduce the stability of an activated species more than expected based upon its basicity alone.

It has previously been noted that both basicity and steric hindrance properties of a base may play a role in its ability to cause epimerization in peptide synthesis (L. Carpino and A. El-Faham, "Effect of Teriary Bases on O-Benzotriazolyuronium Salt-Induced Peptide Segment Coupling," *J. Org. Chem.*, vol. 59, pp. 695-698, 1994). Therefore, an important feature of the present invention is that it identifies a key variable in a carbodiimide coupling process affecting stability of activated amino acid species at elevated temperatures, and that it provides an improved method which uniquely improves synthesis quality with only a minimal amount of base present. Minimizing the amount of the base thereby limits generation of other nucleophiles which could otherwise quickly react with and destroy an electrophilic activated species at elevated temperatures.

To further investigate the role of base during the coupling reaction a known very difficult coupling reaction was explored; specifically, coupling an Fmoc-Aib-OH residue onto another Aib residue, a reaction previously explored by Tofteng, supra. We were able to reproduce Tofteng's results and achieve a 92% purity with a 20 min coupling at 75° C. As an improvement, however, we were able to nearly match this result in only 6 minutes at 90° C. in the presence of 0.1 equivalent of DIEA. The presence of 0.1 equivalents of DIEA was superior to both 0 and 1.0 equivalents of DIEA at each coupling time tested; e.g., Table 5 and FIG. 10 (in which the base is the main variable; all of the reactions having been carried out at either 90° C. or 100° C.). These results show that less than 1 equivalent of a base is uniquely suited for elevated temperature coupling because it provide an optimal balance between the stability of the activated amino acid and a basic environment for accelerating acylation.

TABLE 5

Coupling Fmoc-Aib-OH onto
Aib-Ile-Asp(OtBu)-Tyr(tBu)-Ile-Asn(Trt)-Gly-$NH_2$
under various conditions

| Entry | Coupling Temp (° C.) | Coupling Time (min) | Base (Equivalents) | % Purity (UPLC-MS) |
|---|---|---|---|---|
| 1 | 75 | 20 | None | 92 |
| 2 | 90 | 2 | None | 30 |
| 3 | 90 | 2 | DIEA-(0.1) | 53 |
| 4 | 90 | 2 | DIEA-(1.0) | 24 |
| 5 | 90 | 4 | None | 65 |
| 6 | 90 | 4 | DIEA-(0.1) | 68 |
| 7 | 90 | 4 | DIEA-(1.0) | 62 |
| 8 | 90 | 6 | None | 73 |
| 9 | 90 | 6 | DIEA-(0.1) | 76 |
| 10 | 90 | 6 | DIEA-(1.0) | 72 |
| 11 | 100 | 6 | DIEA-(0.1) | 89 |
| 12 | 100 | 10 | None | 86 |
| 13 | 100 | 10 | DIEA-(0.1) | 93 |
| 14 | 100 | 10 | DIEA-(1.0) | 85 |

Experiment Conditions:
Peptide Sequence=Fmoc-Aib-Aib-IDYING-$NH_2$
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method=1 min at 90° C.
Washing=Post-Deprotection (2 mL, 2 mL, 3 mL-DMF); Post-Coupling=None
Coupling=5-fold excess of AA/DIC/Oxyma (1:1:1) in 4 mL solution
Cleavage=5 mL of TFA/TIS/$H_2O$/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

Cysteine

It is well documented that conversion of an amino acid to an activated ester increases the acidity of the alpha (α)-carbon's proton. Cysteine derivatives are particularly susceptible to epimerization due to the electron withdrawing effect of the side chain sulfur atom as shown in FIG. 11. Significant epimerization of cysteine has been observed under elevated temperature coupling conditions using onium salt activation strategies. Replacing DIEA or NMM with the more hindered base TMP has been shown to reduce epimerization levels for cysteine during HBTU coupling (Palasek). TMP appears less effective, however, for difficult couplings and is not recommended as a standard replacement for DIEA. Reducing coupling temperature to 50° C. or less has reduced, but not eliminated, cysteine epimerization. The lower temperature is not ideal, however, because a lower coupling temperature can result in incomplete coupling and longer reaction time. Recently, Collins et al (J. Collins, K. Porter, S. Singh and G. Vanier, "High-Efficiency Solid Phase Peptide Synthesis (HE-SPPS)," *Org. Lett.*, vol. 16, pp. 940-943, 2014) it showed that the use of a carbodiimide based activation method without the presence of any base (DIC/Oxyma) minimized cysteine epimerization even at coupling temperatures as high as 90° C. The inventors have discovered, however, that a small amount of base can be added to this same process without significantly increasing cysteine epimerization (Table 6, entries 2 and 6). This was tested on the same peptide sequence previously studied by Palasek and Collins et al (J. Collins, K. Porter, S. Singh and G. Vanier, "High-Efficiency Solid Phase Peptide Synthesis (HE-SPPS)," *Org. Lett.*, vol. 16, pp. 940-943, 2014) which contains a cysteine coupling and is susceptible to epimerization. Table 6 summarizes these results.

TABLE 6

Cysteine Epimerization during ABC 20mer synthesis under various carbodiimide coupling conditions

| Entry | Coupling Temp (° C.) | Coupling Time | Base (Equivalents) | % Purity (UPLC-MS) | % D-Cys |
|---|---|---|---|---|---|
| 1 | 90 | 2 | None | 72 | 0.69 |
| 2 | 90 | 2 | DIEA-(0.1) | 78 | 1.46 |
| 3 | 90 | 4 | DIEA-(0.1) | 74 | Not measured |
| 4 | 90 | 2 | DIEA-(1.0) | 51 | 3.91 |
| 5 | 90 | 2 | NMM-(2.0) | 68 | 8.65 |
| 6 | 100 | 2 | DIEA-(0.1) | 76 | 0.85 |

Experiment Conditions:
Peptide Sequence (ABC 20mer)=VYWTSPFMKLIHEQC-NRADG-$NH_2$
Synthesis Scale=0.1 mmol
Resin=Rink Amide MBHA Polystyrene Resin (0.38 mmol/g)
Instrument=Liberty Blue Microwave Peptide Synthesizer (CEM Corp., Matthews, N.C.)
Deprotection=3 mL of a 10% (w/v) Piperazine in EtOH: NMP (1:9)
Microwave Deprotection Method=1 min at 90° C.
Washing=Post-Deprotection (2 mL, 2 mL, 3 mL-DMF); Post-Coupling=None
Coupling=5-fold excess of AA/DIC/Oxyma (1:1:1) in 4 mL solution
Cleavage=5 mL of TFA/TIS/$H_2O$/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)
Epimerization Analysis=GC-MS after hydrolysis/derivatization w/deuterium labeling (C.A.T. GmbH)

Arginine

It is well known that during the coupling reaction the nucleophilic side chain of arginine is susceptible to forming a δ-lactam [M. Cezari and L. Juliano, "Studies on lactam formation during coupling procedures of N alpha z-N omega-protected arginine derivatives," *J Pept. Res.*, vol. 9, pp. 88-91, 1996]. Activating the carboxylic acid promotes attack by the highly basic δ-guanidino group (pKa=12.5) as shown in FIG. 12. This irreversible reaction converts an activated arginine derivative into an inactive species by ejecting the activator. This intramolecular side reaction increases at elevated temperatures leading to significant arginine deletion (P. White, J. Collins and Z. Cox, "Comparative study of conventional and microwave assisted synthesis," in 19*th American Peptide Symposium*, San Diego, Calif., 2005). As a potential alternative, arginine can be coupled at room temperature for a long initial period (e.g., about 30 minutes) followed by a shorter time at a higher temperature; J. Collins, "Microwave-Enhanced Synthesis of Peptides, Proteins, and Peptidomimetics," in *Microwaves in Organic Synthesis 3rd Ed.*, Weinheim, Germany, Wiley-VCH Verlag & Co. KGaA, 2013, pp. 897-960. This method is disadvantageously slow, however, and requires twice as much arginine because the coupling must be repeated.

In contrast, the invention provides previously undocumented advantages of carbodiimide coupling methods at high temperatures for arginine coupling. In particular, arginine can be coupled at very high temperatures (up to 90° C.) without significant δ-lactam formation using standard carbodiimide coupling chemistry. This appears to be due to the more acidic coupling environment of standard carbodiimide coupling methods which reduce the propensity of nucleophilic attack by the nucleophilic arginine side chain. A similar effect has been observed with a cyclization reaction of an ornithine derivative in the presence of base with both DIC/HOBt/DIEA (1:1:1) and PyBOP/DIEA activation systems (T. Lescrinier, R. Busson, H. Winter, C. Hendrix, G. Janssen, C. Pannecouque, J. Rozenski, A. Aerschot and P. Herdewijn, "a-Amino acids derived from ornithine as building blocks for peptide synthesis," *J. Pept. Res.*, vol. 49, pp. 183-189, 1997). The inventors noted that eliminating the base from the activation method was beneficial in eliminating the intramolecular side reaction. As a particular advantage, adding only a small amount of base still allowed arginine to be coupled at 90° C. without significant δ-lactam formation. Because the amount of base added was minimal, the overall pH was lower than in standard onium salt coupling methods. The less basic conditions allowed the resulting coupling behavior to mimic standard carbodiimide coupling chemistry in regards to δ-lactam formation, while simultaneously providing the other benefits of this coupling method.

TABLE 7

Synthesis of ABRF 1992 peptide with known δ-Lactam Formation side reaction

| Entry | Activation Method | Coupling Temp (° C.) | Coupling Time (min) | Base (Equivalents) | % Purity (UPLC-MS) |
|---|---|---|---|---|---|
| 1 | HBTU/DIEA (0.9:2) | 90 | 2 | DIEA-(2) | 37 |
| 2 | DIC/Oxyma (1:1) | 90 | 2 | None | 87 |
| 3 | DIC/Oxyma (1:1) | 90 | 2 | DIEA-(0.1) | 82 |
| 4 | DIC/Oxyma (1:1) | 100 | 2 | DIEA-(0.1) | 78 |

Experiment Conditions:
Peptide Sequence (ABRF 1992)=GVRGDKGNPGWPGAPY
Synthesis Scale=0.1 mmol
Resin=Fmoc-Tyr(tBu)-Wang Resin (0.64 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method=1 min at 90° C.
Washing=Post-Deprotection (2 mL, 2 mL, 3 mL-DMF); Post-Coupling=None
Coupling=5-fold excess of amino acid in 4 mL solution
Cleavage=5 mL of TFA/TIS/H$_2$O/DODt (92.5:2.5:2.5:2.5) for 30 min at 38° C. in an Accent MW cleavage system (CEM Corp., Matthews, N.C.)
Analysis (entry 1)=Peptide was analyzed on a Waters Atlantis C18 column (2.1×150 mm) at 214 nm with a gradient of 5-70% MeCN (0.1% formic acid), 0-20 min. Mass analysis was performed using an LCQ Advantage ion trap mass spectrometer with electrospray ionization (Thermo Electron).
Analysis (entry 2-4)=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

FIGS. 13-16 reflect data from the experiments listed in Table 7. In particular, FIG. 13 illustrates the relatively poor results at elevated temperatures using 2 equivalents of base, while FIG. 16 illustrates the much better results at the same temperature using 0.1 equivalent of base.

The invention's modification to carbodiimide based activation raises the pH to avoid undesirable features of carbodiimide based coupling such as premature cleavage of hyper-acid sensitive linkers at elevated temperature. By only adding a small amount of base, however, the unique properties of a carbodiimide based coupling are maintained (long lifetime of activated ester, minimal epimerization of cysteine derivatives, and avoidance of δ-lactam formation of arginine derivatives). This is because the overall pH of the coupling reaction is kept closer to 7—which is ideal for avoiding both basic and acidic catalyzed side reactions—while simultaneously raising the pH somewhat, which increases the rate of acylation.

Hyper-Acid Sensitive Linkers

Hyper-acid sensitive linkers such as 2-chlorotrityl and Trityl in SPPS have the capacity to overcome key side reactions and to generate fully protected peptide fragments useful in peptide condensation reactions. Nevertheless, premature cleavage of these linker bonds is a concern at higher temperatures due to their increased lability. Common activators used in SPPS (HOBt, HOAt, 6-Cl-HOBt, Oxyma) are acidic and can act like common cleavage acids (e.g., acetic acid) and cleave the peptide-resin bond prematurely; R. E.-F. A. a. A. F. Subirós-Funosas, "Use of Oxyma as pH modulatory agent to be used in the prevention of base-driven side reactions and its effect on 2-chlorotrityl chloride resin," *Pept. Sci.*, vol. 98, pp. 89-97, 2012. Higher temperatures tend to increase the premature cleavage from acidic activator additives.

Standard carbodiimide coupling chemistry at elevated temperatures up to 60° C. has successfully avoided premature cleavage. Friligou et al (I. Friligou, E. Papadimitriou, D. Gatos, J. Matsoukas and T. Tselios, "Microwave-assisted solid-phase peptide synthesis of the 60-110 domain of human pleiotrophin on 2-chlorotrityl resin," *Amino Acids*, vol. 40, pp. 1431-1440, 2011) described a successful synthesis of a 51 mer peptide with DIC/HOBt (1:1) activation for 5 min at 60° C. *maximum* temperature. The desired product was obtained in 30 hours at 60% crude purity and 51% crude yield. Accordingly, limiting the temperature to 60° C. or less appears to avoid premature coupling when using hyper-acid sensitive resins; J. Collins, "Microwave-Enhanced Synthesis of Peptides, Proteins, and Peptidomimetics," in *Microwaves in Organic Synthesis* 3rd Ed., Weinheim, Germany, Wiley-VCH Verlag & Co. KGaA, 2013, pp. 897-960.

Limiting the coupling temperature to 60° C., however, has two main disadvantages. First, the 60° C. temperature may not provide enough energy to complete difficult couplings. Second, coupling at lower temperatures requires longer reaction times thereby significantly increasing the total synthesis time. As an example, the method of Friligou et al resulted in low purity when synthesizing the difficult Thymosin peptide (Table 2, entry 1-2). Synthesizing this same peptide using a coupling temperature of 90° C., however, resulted in a significantly higher crude purity and a reduced synthesis time. Therefore, a method that allows for higher temperatures at higher yields using hyper-acid sensitive linkers would be of significant value.

The inventors have discovered that adding small amounts of base significantly enhances the yield of the well-known [65-74]ACP peptide when synthesized on a 2-chlorotrityl linker at 90° C. (Table 8). The addition of 0.1 equivalents of DIEA increased the yield 134% for DIC/HOBt and 176% for DIC/Oxyma activation.

TABLE 8

Improved Yield for the 2-chlorotrityl linker with the addition of base to Carbodiimide Based Couplings at Elevated Temperature

| Entry | Activation Method | Coupling Temp (° C.) | Coupling Time (min) | Base (Equivalents) | % Purity (UPLC-MS) | Yield |
|---|---|---|---|---|---|---|
| 1 | DIC/HOBt (1:1) | 60 | 5 | None | 89 | 91 |
| 2 | DIC/HOBt (1:1) | 60 | 5 | DIEA-(0.1) | 89 | 92 |
| 3 | DIC/HOBt (1:1) | 90 | 2 | None | 87 | 29 |
| 4 | DIC/HOBt (1:1) | 90 | 2 | DIEA-(0.1) | 92 | 68 |
| 5 | DIC/Oxyma (1:1) | 90 | 2 | None | 86 | 17 |
| 6 | DIC/Oxyma (1:1) | 90 | 2 | DIEA-(0.1) | 91 | 47 |
| 7 | DIC/Oxyma (1:1) | 90 | 2 | DIEA-(0.8) | 91 | 44 |

Experiment Conditions:
Peptide Sequence ([65-74]ACP)=VQAAIDYING
Synthesis Scale=0.1 mmol
Resin=Fmoc-Gly-2-Chlorotrityl-Resin (0.68 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method=1 min at 90° C.
Washing=Post-Deprotection (2 mL, 2 mL, 3 mL-DMF); Post-Coupling=None
Coupling=5-fold excess of amino acid in 4 mL solution
Cleavage=5 mL of TFA/TIS/H$_2$O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

The inventors have also discovered that adding small amounts of base significantly enhances the yield of the well-known [65-74]ACP peptide when synthesized on a Trityl linker at 90° C. (Table 9). Adding 0.1 equivalents of DIEA resulted in complete stability with both DIC/HOBt and DIC/Oxyma activation. This represents a 35% yield increase for DIC/HOBt and a 153% yield increase for DIC/Oxyma. In general, the Trityl linker appears somewhat more stable than the 2-chlorotrityl linker under these conditions at elevated temperatures.

TABLE 9

Improved Yield for the Trityl linker with the addition of base to Carbodiimide Based Couplings at Elevated Temperature

| Entry | Activation Method | Coupling Temp (° C.) | Coupling Time (min) | Base (Equivalents) | % Purity (UPLC-MS) | Yield |
|---|---|---|---|---|---|---|
| 1 | HBTU/DIEA | Room Temperature | 30 | DIEA-(2.0) | 94 | 98 |
| 2 | DIC/HOBt (1:1) | 90 | 2 | None | 93 | 72 |
| 3 | DIC/HOBt (1:1) | 90 | 2 | DIEA-(0.1) | 95 | 97 |
| 4 | DIC/Oxyma (1:1) | 90 | 2 | None | 90 | 38 |
| 5 | DIC/Oxyma (1:1) | 90 | 2 | DIEA-(0.1) | 95 | 96 |

Experiment Conditions:
Peptide Sequence ([65-74]ACP)=VQAAIDYING
Synthesis Scale=0.1 mmol
Resin=Fmoc-Gly-NovaSyn-TGT-Resin (0.19 mmol/g)
Instrument=Liberty Blue Microwave Peptide Synthesizer (CEM Corp., Matthews, N.C.)
Deprotection=3 mL of a 10% (w/v) piperazine in EtOH: NMP (1:9)
Microwave Deprotection Method (entry 1)=5 min+10 min at room temperature
Microwave Deprotection Method (entries 2-6)=1 min at 90° C.
Washing (entry 1)=Post-Deprotection (5×5 mL-DMF); Post-Coupling=(5×5 mL-DMF)
Washing (entries 2-6)=Post-Deprotection (2 mL, 2 mL, 3 mL-DMF); Post-Coupling=None
Coupling=5-fold excess of amino acid in 4 mL solution
Cleavage=5 mL of TFA/TIS/H$_2$O/DODt (92.5:2.5:2.5:2.5) for 30 min at 38° C. in an Accent MW cleavage system (CEM Corp., Matthews, N.C.)
Analysis=Peptides were analyzed on a Waters UPLC ACQUITY H-Class with 3100 Single Quad MS using acetonitrile/water with 0.1% TFA as the solvent system on C18 Column (1.7 mm, 2.1×100 mm)

Tables 10 and 11 summarize the comparative advantages of the invention.

TABLE 10

Comparison of Carbodiimide and Onium Salt Activation Strategies for Peptide Coupling at Elevated Temperature

| Feature | NEW METHOD DIC/Oxyma/DIEA (1:1:0.1) | STANDARD CARBODIIMIDE DIC/Oxyma (1:1) | ONIUM SALTS [Aminium] HBTU/DIEA (0.9:2) | ONIUM SALTS [Phosphonium] PyBOP/DIEA (1:2) |
|---|---|---|---|---|
| Coupling Time Required | FASTEST | FAST | LONGER-Temperature limited | LONGER-Temperature limited |
| Synthesis Purity | HIGHEST | HIGH | MODERATE | MODERATE |
| Pre-activation required | NO | NO | NO* (w/slight deficit) | NO |

TABLE 10-continued

Comparison of Carbodiimide and Onium Salt Activation Strategies for Peptide Coupling at Elevated Temperature

| Feature | NEW METHOD DIC/ Oxyma/ DIEA (1:1:0.1) | STANDARD CAR-BODIIMIDE DIC/Oxyma (1:1) | ONIUM SALTS | |
|---|---|---|---|---|
| | | | [Aminium] HBTU/ DIEA (0.9:2) | [Phosphonium] PyBOP/DIEA (1:2) |
| Stability of activated ester formed | GOOD | BEST | LIMITED | LIMITED |
| Epimerization of Cysteine derivatives | OK | OK | BAD | BAD |
| σ-lactam formation of Arginine | OK | OK | BAD | BAD |
| Stability of hyper-acid sensitive resins | YES | NO | YES | YES |
| Stability of activator reagents in solution | GOOD | GOOD | LESS STABLE | LESS STABLE |

TABLE 11

Comparison of Carbodiimide Activation Strategies for Peptide Coupling at Elevated Temperature

| Feature | NEW METHOD DIC/ Oxyma/ DIEA (1:1:0.1) | STANDARD CARBODIIMIDE DIC/Oxyma (1:1) | CARBODIIMIDE w/Full Base Equivalent DIC/Oxyma/DIEA (1:1:1) or (1:1:2) |
|---|---|---|---|
| Coupling Time Required | FASTEST | FAST | LONGER-Temperature Limited |
| Synthesis Purity | HIGHEST | HIGH | HIGH/MODERATE |
| Pre-activation required | NO | NO | PREFERABLE- (except cysteine and arginine) |
| Stability of activated ester formed | GOOD | BEST | LOW |
| Epimerization of Cysteine derivatives | OK | OK | BAD |
| σ-lactam formation of Arginine | OK | OK | BAD |
| Stability of hyper-acid sensitive resins | YES | NO | YES |
| Stability of activator reagents in solution | GOOD | GOOD | GOOD |

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A method for coupling amino acids into peptides or peptidomimetics, the improvement comprising:
combining an amino acid, a carbodiimide, an activator additive, and a base, with the base in an amount of less than 1 equivalent compared to the amino acid to be activated; and carrying out the activation and coupling at a temperature greater than 30° C.

2. The method according to claim 1 carried out within a total coupling time less than 10 minutes.

3. The method according to claim 1 carried out within a total coupling time less than 4 minutes.

4. The method according to claim 1 carried out within a total coupling time less than 2 minutes.

5. The solid phase peptide synthesis method according to claim 1.

6. The method according to claim 5 wherein the base is selected from the group consisting of DIEA, NMM, TMP, TEA and combinations thereof.

7. The method according to claim 5 wherein the amount of base is no more than 0.2 equivalent based on the amount of amino acid present.

8. The method according to claim 5 wherein the amount of base is no more than 0.1 equivalent based on the amount of amino acid present.

9. The method according to claim 5 wherein the carbodiimide is selected from the group consisting of DCC, DIC, EDC, and mixtures thereof.

10. The method according to claim 9 wherein the activator additive is selected from the group consisting of HOBt, HOAt, 6-Cl-HOBt, Oxyma, NHS and mixtures thereof.

11. The method according to claim 5 wherein the activation and coupling are carried out at temperature of between about 30° C. and 110° C.

12. The method according to claim 5 wherein the activation and coupling are carried out at temperature of at least about 60° C.

13. The method according to claim 5 wherein the activation and coupling are carried out at temperature of at least about 75° C.

14. The method according to claim 5 wherein the activation and coupling are carried out at temperature of at least about 90° C.

15. The method according to claim 1 wherein the amino acid is selected from the group consisting of essential amino acids, conditionally essential amino acids and dispensable amino acids.

16. A method for coupling carboxylic acids and amines, the improvement comprising: combining a carboxylic acid, an amine, a carbodiimide, an activator additive, and a base, with the base in an amount of less than 1 equivalent compared to the amine; and carrying out activation and coupling at a temperature greater than 30° C.

17. The method according to claim 16 carried out within a total coupling time less than 10 minutes.

18. The method according to claim 16 carried out within a total coupling time less than 4 minutes.

19. The method according to claim 16 carried out within a total coupling time less than 2 minutes.

20. The solid phase peptide synthesis method according to claim 16.

21. The method according to claim 20 wherein the base is selected from the group consisting of DIEA, NMM, TMP, TCA and combinations thereof.

22. The method according to claim 20 wherein the amount of base is no more than 0.2 equivalent based on the amount of amine present.

23. The method according to claim 20 wherein the amount of base is no more than 0.1 equivalent based on the amount of amine acid present.

24. The method according to claim 20 wherein the carbodiimide is selected from the group consisting of DCC, DIC, EDC, and mixtures thereof.

25. The method according to claim 24 wherein the activator additive is selected from the group consisting of HOBt, HOAt, 6-Cl-HOBt, Oxyma, NHS and mixtures thereof.

26. The method according to claim 20 wherein the activation and coupling are carried out at temperature of between about 30° C. and 110° C.

27. The method according to claim 20 wherein the activation and coupling are carried out at temperature of at least about 60° C.

28. The method according to claim 20 wherein the activation and coupling are carried out at temperature of at least about 75° C.

29. The method according to claim 20 wherein the activation and coupling are carried out at temperature of at least about 90° C.

30. A solid phase method for coupling amino acids into peptides or peptidomimetics, the improvement comprising: combining a hyper-acid sensitive linker connecting a peptide and a resin, an amino acid, a carbodiimide, an activator additive, and a base, with the base is present in an amount of less than 1 equivalent compared to the amino acid to be activated; and carrying out the activation and coupling at a temperature greater than 30° C.

31. The method according to claim 30 in which the base is present in an amount of 0.2 equivalent compared to the amino acid to be activated.

32. The method according to claim 30 in which the base is present in an amount of 0.1 equivalent compared to the amino acid to be activated.

33. The method according to claim 30 in which the linker is selected from the group consisting of 2-chlorotrityl and Trityl.

34. The method according to claim 30 in which the carbodiimide is selected from the group consisting of DCC, DIC, EDC, and mixtures thereof.

35. The method according to claim 30 in which the activator additive is selected from the group consisting of HOBt, HOAt, 6-Cl-HOBt, Oxyma, NHS and mixtures thereof.

36. The method according to claim 30 in which the activation and coupling are carried out at a temperature of between about 90° C. and 110° C.

* * * * *